US 8,510,850 B2

(12) United States Patent
Dove et al.

(10) Patent No.: US 8,510,850 B2
(45) Date of Patent: Aug. 13, 2013

(54) FUNCTIONALITY FOR PROVIDING DE-IDENTIFIED DATA

(75) Inventors: Bryan J. Dove, Seattle, WA (US); Craig F. Feied, Kirkland, WA (US); Michael T. Gillam, Silver Spring, MD (US); Jonathan A. Handler, Northbrook, IL (US); Dobroslav K. Kolev, Vienna, VA (US); Kurt Arley Luke Thorne, Hyattsville, MD (US)

(73) Assignee: Microsoft Corporation, Redmond, WA (US)

( * ) Notice: Subject to any disclaimer, the term of this patent is extended or adjusted under 35 U.S.C. 154(b) by 223 days.

(21) Appl. No.: 12/970,984

(22) Filed: Dec. 17, 2010

(65) Prior Publication Data

US 2012/0159637 A1 Jun. 21, 2012

(51) Int. Cl.
 *G06F 21/00* (2006.01)
(52) U.S. Cl.
 USPC .................................................. 726/26
(58) Field of Classification Search
 USPC ................................................. 726/26–30
 See application file for complete search history.

(56) References Cited

U.S. PATENT DOCUMENTS

| | | | |
|---|---|---|---|
| 7,519,591 B2 | 4/2009 | Landi et al. | |
| 2004/0193901 A1* | 9/2004 | Bharara | 713/193 |
| 2005/0193207 A1* | 9/2005 | Buck | 713/178 |
| 2005/0236474 A1 | 10/2005 | Onuma et al. | |
| 2007/0260492 A1 | 11/2007 | Feied et al. | |
| 2008/0147554 A1 | 6/2008 | Stevens et al. | |
| 2010/0042583 A1 | 2/2010 | Gervais et al. | |
| 2012/0151597 A1* | 6/2012 | Gupta et al. | 726/26 |

OTHER PUBLICATIONS

Sokolova, et al., "Personal Health Information Leak Prevention in Heterogeneous Texts," retrieved at <<http://acl.eldoc.ub.rug.nl/mir ror/W/W09/W09-4109.pdf>>, Proceedings of the Workshop on Adaptation of Language Resources and Technology to New Domains, 2009, pp. 58-69.
Douglass, et al., "De-Identification Algorithm for Free-Text Nursing Notes," retrieved at <<http://cinc.mit.edu/archives/2005/pdf/0331. pdf>>, Computers in Cardiology, 2005, 4 pages.
Vankooy, Mark, "HIMSS USA—quick blog (Amalga UIS at Virtua)," retrieved at <<http://blogs.msdn.com/b/hitwurkz/archive/ 2010/02/28/himss-usa-quick-blog-amalga-uis-at-virtua.aspx>>, AllUpHealthIT, MSDN, Microsoft Corporation, Redmond, Washington, Feb. 28, 2010, 1 page.
"HL7 V2.X prose based parser," retrieved at <<http://code.msdn. microsoft.com/HL7v2parser>>, MSDN, Microsoft Corporation, Redmond, Washington, May 11, 2010, 1 page.
"Amalga Products," retrieved at <<http://www.microsoft.com/ amalga/products/products-overview.mspxMicrosoft Amalga>>, retrieved on Dec. 16, 2010, Microsoft Amalga, Microsoft Corporation, Redmond, Washington, 1 page.

\* cited by examiner

*Primary Examiner* — Brandon Hoffman
*Assistant Examiner* — Anthony Brown

(57) ABSTRACT

A de-identification system is described herein for converting original messages into de-identified messages. The de-identification system leverages original message-inception-functionality which operates as a gateway for providing original messages for use by a production environment. Namely, the de-identification system includes a transformation module that receives the original messages from the original message-inception functionality. The transformation module then converts instances of sensitive information contained in the original messages into non-sensitive information, to produce the de-identified messages. A de-identified environment can consume the de-identified messages with high confidence that the messages have been properly sanitized. This is because the de-identification work has been performed at a well-contained quarantine level of the message processing functionality.

20 Claims, 13 Drawing Sheets

FUNCTIONALITY FOR PROVIDING DE-IDENTIFIED DATA

BACKGROUND

Computer systems often maintain records that contain sensitive information regarding various entities. For example, a computer system that operates in a health-related domain may provide records which contain personal information regarding patients. A computer system that operates in a financial domain may provide records which contain personal information regarding account holders, and so on. Individuals who have authorized access to these records are referred to herein as trusted entities, or honest brokers. These computer systems typically provide appropriate security provisions to prevent the release of the sensitive information to unauthorized entities.

At the same time, there is sometimes a legitimate need to make the above-described types of records available outside the normal production domains of the computer systems. To cite one example, a trusted entity may wish to allow an external researcher to perform analysis on the basis of the records. This will allow the external researcher to identify trends and make other statistical conclusions on the basis of the records. This type of access raises various challenges, however, as the trusted entity may be bound by contractual obligations to preserve the privacy of the sensitive information. Further, an applicable jurisdiction may have enacted laws which prevent the dissemination of the sensitive information, such as the Health Insurance Portability and Accountability Act (HIPAA) in the United States.

To address these concerns, the trusted entity may remove or otherwise obscure the sensitive information within the records. According to the terminology used herein, this general process is referred to as de-identification, and the records produced thereby are referred to as de-identified data. If performed correctly, the de-identified data will not reveal any sensitive information regarding the entities associated with the records.

However, for reasons set forth in greater detail herein, there is a risk that the process of de-identification is not performed correctly. This may result in the release of sensitive information to unauthorized recipients. This outcome, in turn, may subject the trusted entity to considerable penalties, ranging from loss of business to legal action.

SUMMARY

A de-identification system is described in which original message-inception functionality serves as a central gateway through which a production environment receives original messages that originate from various information sources. The de-identification system also employs a transformation module which converts the original messages into de-identified messages, for storage in de-identified message-inception functionality. The de-identified messages are counterparts of the original messages, producing by "sanitizing" sensitive information within the original messages. A de-identified environment then receives the de-identified messages from the de-identified message-inception functionality. As used herein, the term production environment corresponds to an environment in which revelation of sensitive information is permitted. The term de-identified environment corresponds to an environment in which revelation of the sensitive information is not permitted.

According to one illustrative feature, the original message-inception functionality includes at least one message queue for storing the original messages. Similarly, the de-identified message-inception functionality includes at least one message queue for storing the de-identified messages. A message queue herein refers to any storage mechanism for storing messages.

A quarantine domain is formed by the original message-inception functionality, the transformation module, and the de-identified message-inception functionality. The quarantine domain serves as a dissemination point for providing both original messages to the production environment and de-identified messages to the de-identified environment. Using this approach, the de-identification system can ensure with high confidence that sensitive information has been properly removed from all of the data that is processed in the de-identified environment. This is because the appropriate de-identification work has been performed on the original messages within the well-contained quarantine domain, prior to any downstream manipulation of the data within the production environment. De-identification that is performed subsequent to such downstream manipulation would be problematic for the reasons set forth herein.

This Summary is provided to introduce a selection of concepts in a simplified form; these concepts are further described below in the Detailed Description. This Summary is not intended to identify key features or essential features of the claimed subject matter, nor is it intended to be used to limit the scope of the claimed subject matter.

The same numbers are used throughout the disclosure and figures to reference like components and features. Series 100 numbers refer to features originally found in FIG. 1, series 200 numbers refer to features originally found in FIG. 2, series 300 numbers refer to features originally found in FIG. 3, and so on.

DETAILED DESCRIPTION

This disclosure is organized as follows. Section A describes an illustrative de-identification system for transforming original data into de-identified data. Section B describes illustrative methods which explain the operation of the de-identification system of Section A. Section C describes illustrative processing functionality that can be used to implement any aspect of the features described in Sections A and B.

Figure 14:
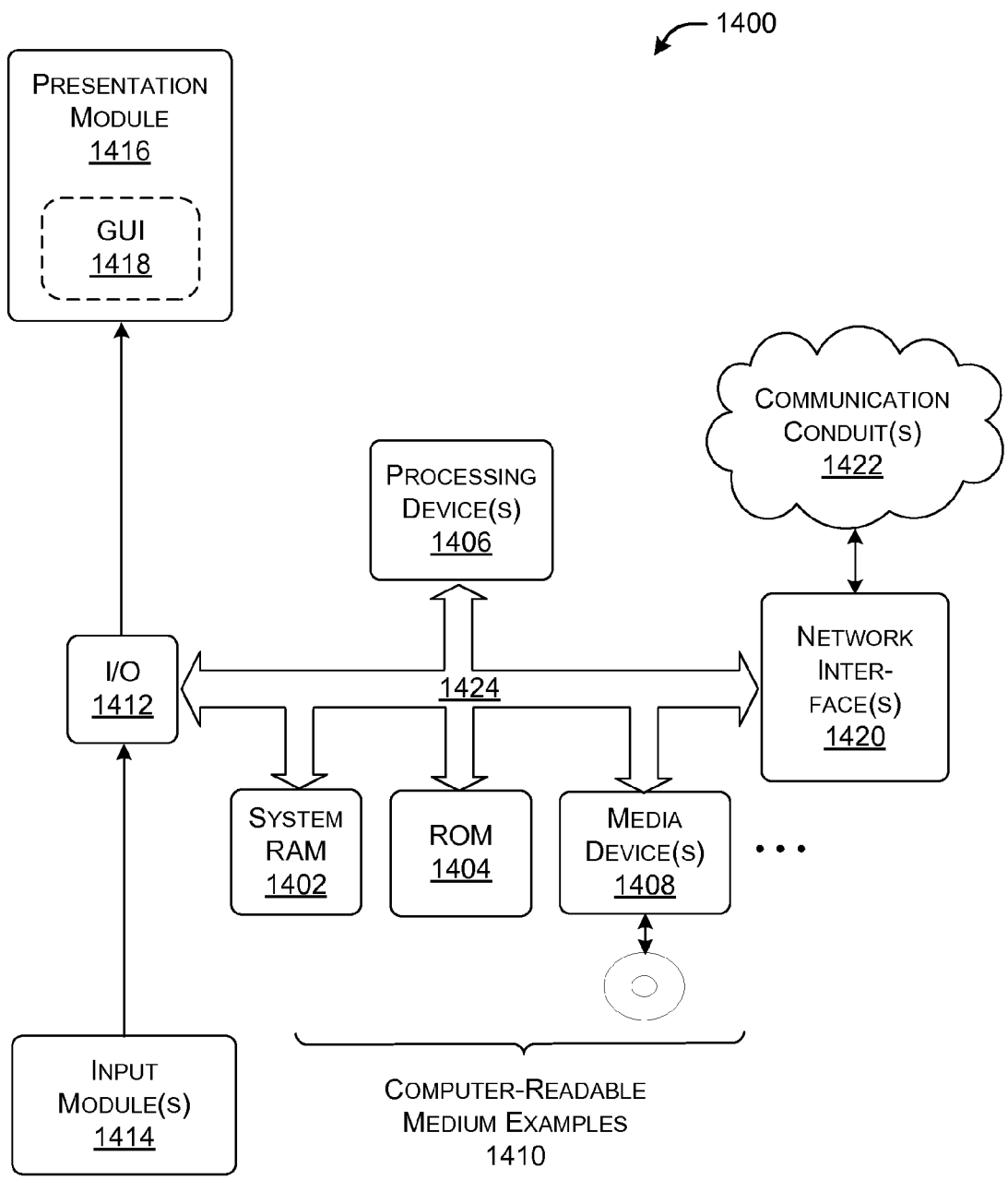
FIG. 14 shows illustrative processing functionality that can be used to implement any aspect of the features shown in the foregoing drawings.

As a preliminary matter, some of the figures describe concepts in the context of one or more structural components, variously referred to as functionality, modules, features, elements, etc. The various components shown in the figures can be implemented in any manner by any physical and tangible mechanisms (for instance, by software, hardware, firmware, etc., and/or any combination thereof). In one case, the illustrated separation of various components in the figures into distinct units may reflect the use of corresponding distinct physical and tangible components in an actual implementation. Alternatively, or in addition, any single component illustrated in the figures may be implemented by plural actual physical components. Alternatively, or in addition, the depiction of any two or more separate components in the figures may reflect different functions performed by a single actual physical component. FIG. 14, to be discussed in turn, provides additional details regarding one illustrative physical implementation of the functions shown in the figures.

Other figures describe the concepts in flowchart form. In this form, certain operations are described as constituting distinct blocks performed in a certain order. Such implementations are illustrative and non-limiting. Certain blocks described herein can be grouped together and performed in a single operation, certain blocks can be broken apart into plural component blocks, and certain blocks can be performed in an order that differs from that which is illustrated herein (including a parallel manner of performing the blocks). The blocks shown in the flowcharts can be implemented in any manner by any physical and tangible mechanisms (for instance, by software, hardware, firmware, etc., and/or any combination thereof).

As to terminology, the phrase "configured to" encompasses any way that any kind of physical and tangible functionality can be constructed to perform an identified operation. The functionality can be configured to perform an operation using, for instance, software, hardware, firmware, etc., and/or any combination thereof.

The term "logic" encompasses any physical and tangible functionality for performing a task. For instance, each operation illustrated in the flowcharts corresponds to a logic component for performing that operation. An operation can be performed using, for instance, software, hardware, firmware, etc., and/or any combination thereof When implemented by a computing system, a logic component represents an electrical component that is a physical part of the computing system, however implemented.

The following explanation may identify one or more features as "optional." This type of statement is not to be interpreted as an exhaustive indication of features that may be considered optional; that is, other features can be considered as optional, although not expressly identified in the text. Similarly, the explanation may indicate that one or more features can be implemented in the plural (that is, by providing more than one of the features). This statement is not be interpreted as an exhaustive indication of features that can be duplicated. Finally, the terms "exemplary" or "illustrative" refer to one implementation among potentially many implementations.

A. Illustrative De-Identification System

Figure 1:
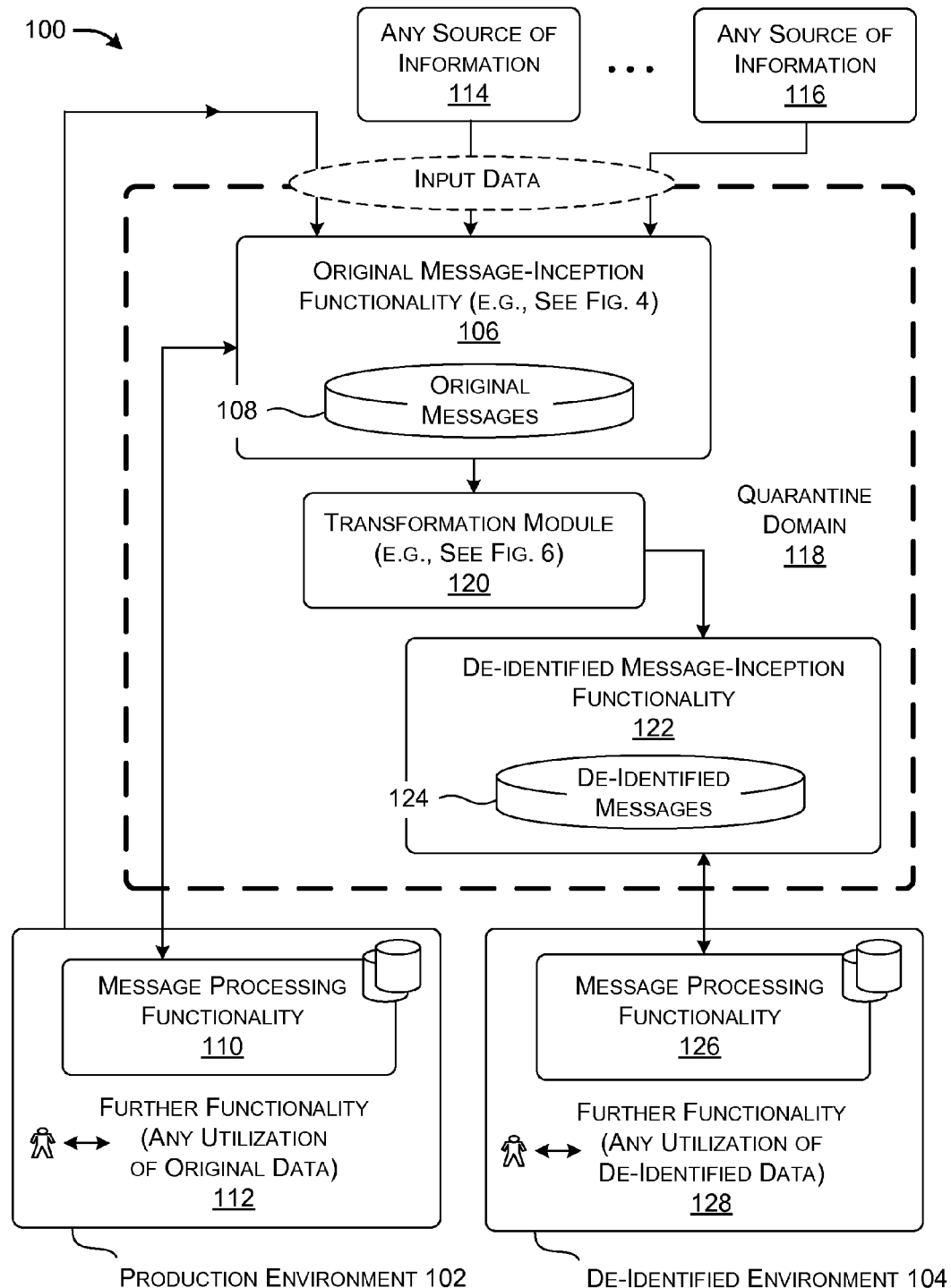
FIG. 1 shows an illustrative de-identification system for producing de-identified data for consumption by a de-identified environment.

FIG. 1 shows a de-identification system 100 that operates to convert data that contains instances of sensitive information to data that contains counterpart instances of non-sensitive information. As used herein, the term sensitive information encompasses any content that any entity wishes to maintain in confidence for any reason or combination of reasons. In a typical scenario, the sensitive information corresponds to personal information regarding individuals. However, in other contexts, the sensitive information can encompass confidential information regarding organizations or other entities. The non-sensitive information, on the other hand, corresponds to content that is not required to be held in confidence. In a healthcare-related domain, for example, non-sensitive information may include clinical data values, medication information, diagnosis information, etc.

The term de-identified data or the like refers to data in which instances of sensitive information have been converted into corresponding instances of non-sensitive information. This de-identified data may alternatively be referred to as sanitized data, scrubbed data, and so on. The following description will explain different ways in which data containing sensitive information can be converted into de-identified data.

FIG. 1 shows two different environments, a production environment 102 and a de-identified environment 104. A production environment 102 corresponds to a setting in which the revelation of sensitive information is permitted. For example, in a healthcare-related context, the production environment 102 corresponds to any functionality for delivering healthcare-related services to patients and/or healthcare providers, etc. In that environment, doctors and other authorized individuals are permitted to view and manipulate sensitive information pertaining to patients. Any such individual is referred to herein as a trusted entity or honest broker. Although FIG. 1 shows only one production environment, the de-identified system 100 can encompass two or more such environments that are permitted to operate on data containing sensitive information.

By contrast, the de-identified environment 104 corresponds to a setting in which the revelation of sensitive information is not permitted for any reason. For example, in a research-related context, the de-identified environment 104 corresponds to any functionality for analyzing a sanitized version of the data used by the production environment 102. In this scenario, researchers are not permitted to view and manipulate sensitive information, e.g., due to contractual prohibitions, statutory prohibitions, etc., or any combination thereof Although FIG. 1 shows only one de-identified production environment, the de-identification system 100 can encompass two or more such environments. For example, other entities which may wish to inspect de-identified data include any party which has a partner relationship with the production environment 102. Other entities that may wish to interact with the de-identified data include government agencies, auditing entities, testers or code-developers, sales representatives who wish to conduct demonstrations, and so on.

In yet other environment-specific scenarios, the de-identification system 100 can provide data that contains at least some sensitive information to various authorized researchers and other authorized individuals. That is, depending on environment-specific considerations, the de-identification system 100 may not be tasked with the responsibility of removing all sensitive information from the original data.

Figure 4:
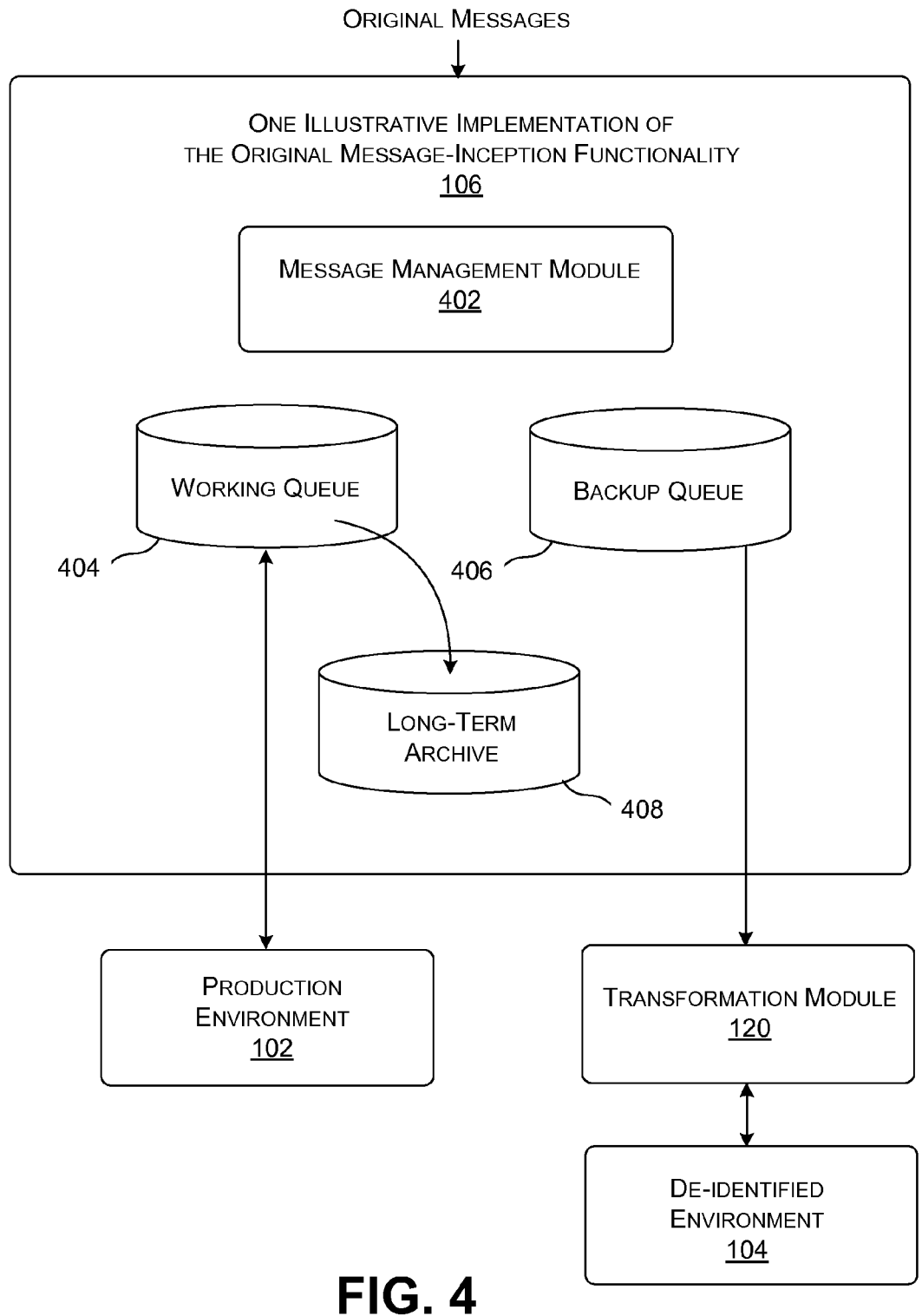
FIG. 4 shows illustrative message-inception functionality for use in the de-identification system of FIG. 1.

According to a first process flow, the production environment 102 receives input data in the form of messages via original message-inception functionality 106. These messages are referred to as original messages herein to emphasize that these messages have not yet been subjected to any downstream processing performed by the production environment 102. More specifically, the original message-inception functionality 106 can receive original messages from one or more sources. The original message-inception functionality 106 can then store the original messages in storage functionality 108. FIG. 4, to be described below in turn, shows one implementation of the original message-inception functionality 106. The production environment 102 then receives the original messages from the original message-inception functionality 106, e.g., by either using a push technique, a pull technique, or combination thereof.

Upon receipt, the production environment 102 can manipulate the data contained in the original messages in any manner. Processing functionality 110 shown in FIG. 1 generically denotes any such manipulation; such processing may including parsing, storage, replication, analysis, etc. The processing functionality 110 produces processed data. Further functionality 112 can make any application-specific use of the processed data. Generally, as mentioned above, the production environment 102 is given access to sensitive information contained within the original messages.

The sources which feed input data to the production environment 102 can include one or more external sources (114, 116, etc.). For example, in a healthcare-related domain, an external source may correspond to a partner lab or the like. That source can formulate messages which contain test results for use in the production environment 102. The original message-inception functionality 106 also receives input data from the production environment 102 itself For example, assume that a user manipulates a record containing personal information. The results of that operation can be formulated as a message. The production environment 102 routes that message to the original message-inception functionality 106, upon which it becomes available to the production environment 102.

In summary, the original message-inception functionality 106 serves as a root gateway through which the production environment 102 receives all of its input data. Further, the data stored at that juncture is data which is in original form, meaning that it has not yet been manipulated by any downstream functionality. However, the terms "original data" and "original messages" can also encompass cases in which the data is substantially in unmodified form.

The de-identification system 100 leverages the use of the original message-inception functionality 106 by also making this mechanism the gateway through which the de-identified environment 104 receives data. In other words, the original message-inception functionality 106 is a component of a quarantine domain 118. All original messages entering the de-identification system 100 effectively pass through the quarantine domain 118 in their original form, where they are stored in the storage functionality 108. The de-identification system 100 then proceeds to sanitize all of the original messages that have been received and stored, creating a de-identified copy of all the original messages. The de-identified environment 104 interacts with the de-identified data provided through this conversion path.

To appreciate the merits of the above-described approach, consider a hypothetical alternative to this approach. Namely, consider the case in which the production environment 102 parses and stores the original data obtained from the original message-inception functionality 106 in one or more databases. Further assume that a trusted entity wishes to produce de-identified data that removes selected sensitive information items from the original data. To perform this task, the trusted entity may identify instances of the target data items in the databases provided by the production environment 102. The trusted entity may then selectively scrub those data items before making the sanitized data as a whole available to the de-identified environment 104.

This approach is problematic for the following reasons. Generally, it may be difficult for the trusted entity to keep track of the processing that has been performed on the original messages within the production environment 102. In view of this, the trusted entity may not be successful in identifying all relevant copies and versions of the sensitive information items in question. For example, the trusted entity may remove sensitive information from one location within a database, not realizing that the sensitive information has been replicated, possibly in another form, in another part of the database. If this is true, the trusted entity can produce de-identified data that contains remnant instances of the sensitive information.

Once again, the de-identification system 100 of FIG. 1 eliminates the above-described concern by drawing all input data in untransformed form from the root gateway, namely the original message-inception functionality 106. The remainder of this description will set forth various implementations of the overarching design principles summarized above.

From a high-level perspective, FIG. 1 indicates that the quarantine domain 118 also includes a transformation module 120 and de-identified message-inception functionality 122. In contrast to the first processing flow described above, the transformation module 120 draws original messages from the original messaging-inception functionality 106. Through various techniques, the transformation module 120 removes all (or some) sensitive information from the original messages to produce de-identified messages. The transformation module 120 can then route the de-identified messages to the de-identified message-inception functionality 122. The de-identified message functionality 122, in turn, stores the de-identified messages in de-identified storage functionality 124. The de-identified environment 104 then receives the de-identified messages from the de-identified message-inception functionality 122. Message processing functionality 126 in the de-identified environment 104 can operate on the de-identified messages to produce processed data; such processing can encompass any type of parsing, storage, replication, analysis, etc. operations. Further functionality 128 can operate on the processed data in any environment-specific manner.

In one scenario, the functionality (126, 128) provided by the de-identified environment 104 is at least a partial replication of the functionality (110, 112) provided in the production environment 102. In this setup, for example, a sales representative can use the "clone" de-identified environment 104 to conduct a demonstration of the similarly-constituted production environment 102. The demonstration will not reveal sensitive information, since all input data that is available to the de-identified environment 104 has been scrubbed in the manner described above. In another case, the functionality (126, 128) provided in the de-identified environment 104 can perform new functions that have no counterpart operations in the production environment 102.

Further, in one scenario, the de-identified environment 104 can process de-identified messages based on the same data flow paradigm used by the production environment 102. In another case, the data flow paradigm used by the de-identified environment 104 can differ from that used in the production environment 102 in any manner.

The transformation module 120 operates by breaking each original message into plural parts, referred to as original message parts. The transformation module 120 then converts each of the original message parts into counterpart transformed message parts. The transformation module 120 can draw on a suite of data de-identifier modules to perform this task. Each of the data de-identifier modules provides a mechanism for transforming a particular type of data item in a particular way.

From a high-level perspective, the various data de-identifier modules provide conversion techniques that can be classified into one or more of categories. The following list identifies representative conversion strategies.

In a first case, a data de-identifier module may pass an original message part through without performing any transformation on it. This may be appropriate in various environment-specific circumstances. For instance, this may be appropriate because the original message part is not regarded as sensitive information.

Moreover, it may be appropriate to retain parts of the original data in unmodified form so that meaningful analysis can be performed on the resultant de-identified data (if, in fact, this is one of the objectives in producing the de-identified data). For example, suppose that a set of original data contains information regarding the diagnoses of patients, lab results, prescribed medications, etc. It may be appropriate to retain this information in untransformed form. By doing so, a researcher can draw meaningful conclusions from the de-identified data, e.g., by identifying trends in maladies being treated at a particular institution. Each controlling entity associated with a particular de-identified environment can identify the information items that are appropriate to preserve, and those that are appropriate to modify.

In addition to the preservation of particular data items, the transformation module 120 may attempt to preserve the structure that is used to organize the data items within an original message. In connection therewith, the transformation module 120 can retain field descriptors or the like (such as XML tags, etc.) which identify the types of fields in an original message, etc.

In a second case, a data de-identifier module can completely obscure an original message part, replacing it with a transformed message part that has no relationship to the original message part. For example, suppose that an original message part conveys a social security number of a patient. A data de-identifier module can delete the social security number and replace it with a completely random number that has no relationship to the original social security number. In another case, a data de-identifier module can delete a patient's actual name and replace it with a fictitious name that has no relation to the original name.

In a third case, a data de-identifier module can apply any rule to the original message part to derive the transformed message part. For example, a data de-identifier module can shift the value of a date by a predetermined amount (in a manner to be described below). This has the benefit of obscuring the actual date without altering its general classification. For example, the data de-identifier module can change the date of birth of an elderly patient in such a manner that the patient will still be regarded as an elderly person. The data de-identifier module can perform the same shifting operation on position data, e.g., by shifting the GPS coordinates of an address to identify a nearby address. This shifting provision allows meaningful conclusions to be drawn based on the de-identified data.

In a fourth case, a data de-identifier module can identify some type of meta-characteristic of an original message part. The data de-identifier module can then replace that original message part with a replacement part that shares the same meta-characteristic. For example, suppose that an original message part identifies a name of a patient. A data de-identifier module can determine the prevalence of this name in one or more databases (such as a census database). The data de-identifier module can then replace the name with a replacement name that has a similar prevalence metric. Otherwise, there may be nothing which links the original name and the replacement name.

Once again, the above-described conversion paradigms are representative, rather than exhaustive.

Figure 2:
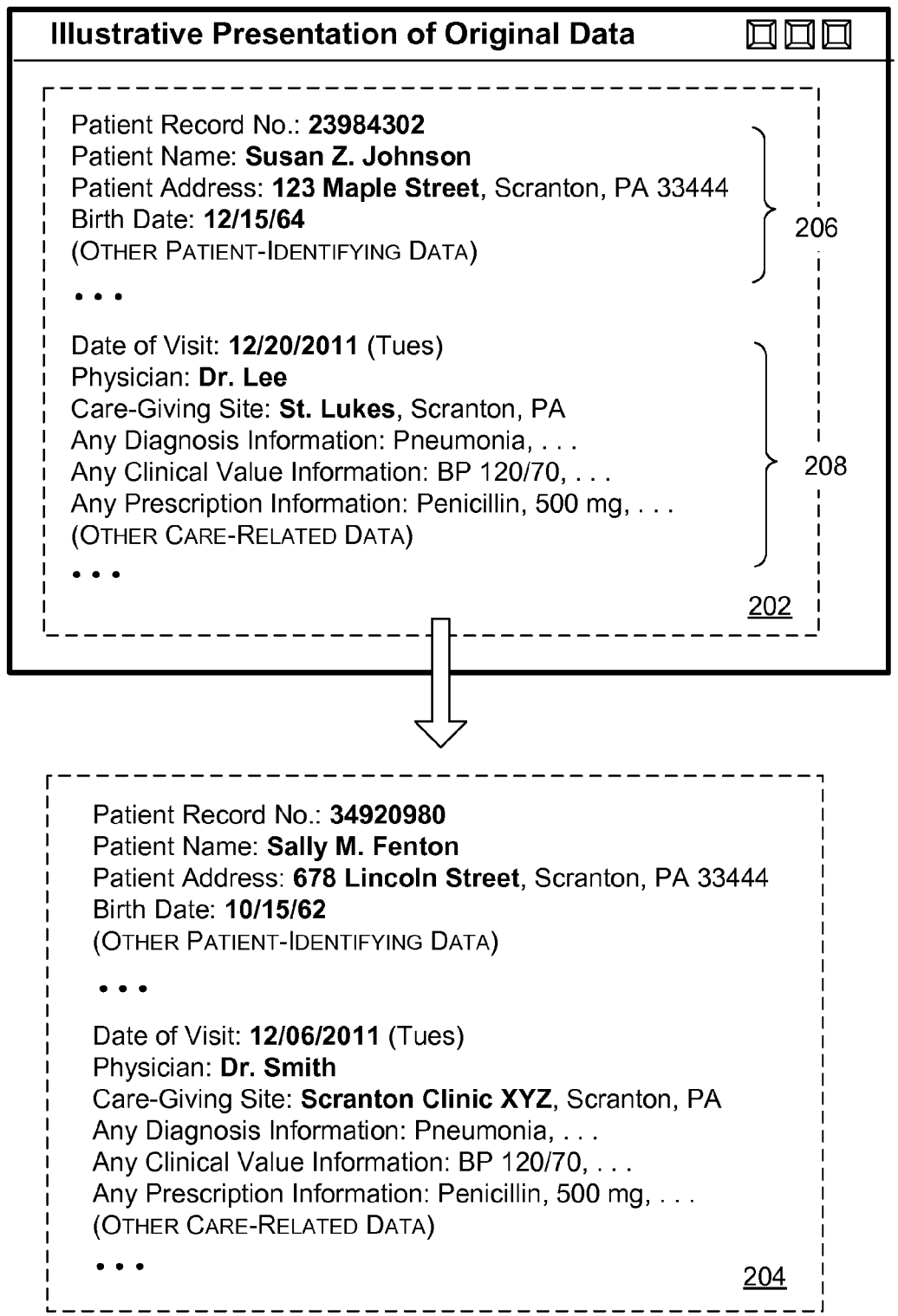
FIG. 2 shows an example of data containing sensitive information and de-identified data containing counterpart non-sensitive information.

Advancing to FIG. 2, this figure is an example which demonstrates how original data 202 can be transformed into de-identified data 204. In this example, the original data 202 pertains to a healthcare-related domain. The original data 202 includes a first series of record fields 206 that provide personal information regarding a patient, such as the patient's ID number, the patient's name, the patient's address, and so on. The original data can also include a second series of record fields 208 that describe treatment received by the patient. It will be appreciated that the nature and organization of these information items are merely representative.

Parts of the original data constitute sensitive information. The transformation module 120 converts these parts into counterpart transformed parts using one or more of the conversion paradigms described above. More generally stated, the transformation module 120 can use an appropriate combination of data identifier modules based on the goals and criteria of a particular de-identification task, as well as the nature of the particular data that is being transformed. To repeat, the transformation module 120 performs such a conversion based on the data as it appears in the original messages, rather than a parsed version of the data in the production environment 102.

For example, the transformation module 120 has replaced the patient ID number with a completely random ID number. The transformation module 120 has also replaced the patient's name with a mock name. However, as noted above, the new name ("Sally M. Fenton") may have the same level of prevalence as the original name ("Susan Z. Johnson"). The transformation module 120 has also modified the birth date of the patient by shifting it a predetermined amount, and so on. By contrast, the transformation module 120 has left information regarding the diagnosis and treatment of the patient in original form. But in other scenarios, any aspect of this diagnosis and treatment information can also be de-identified.

Figure 3:
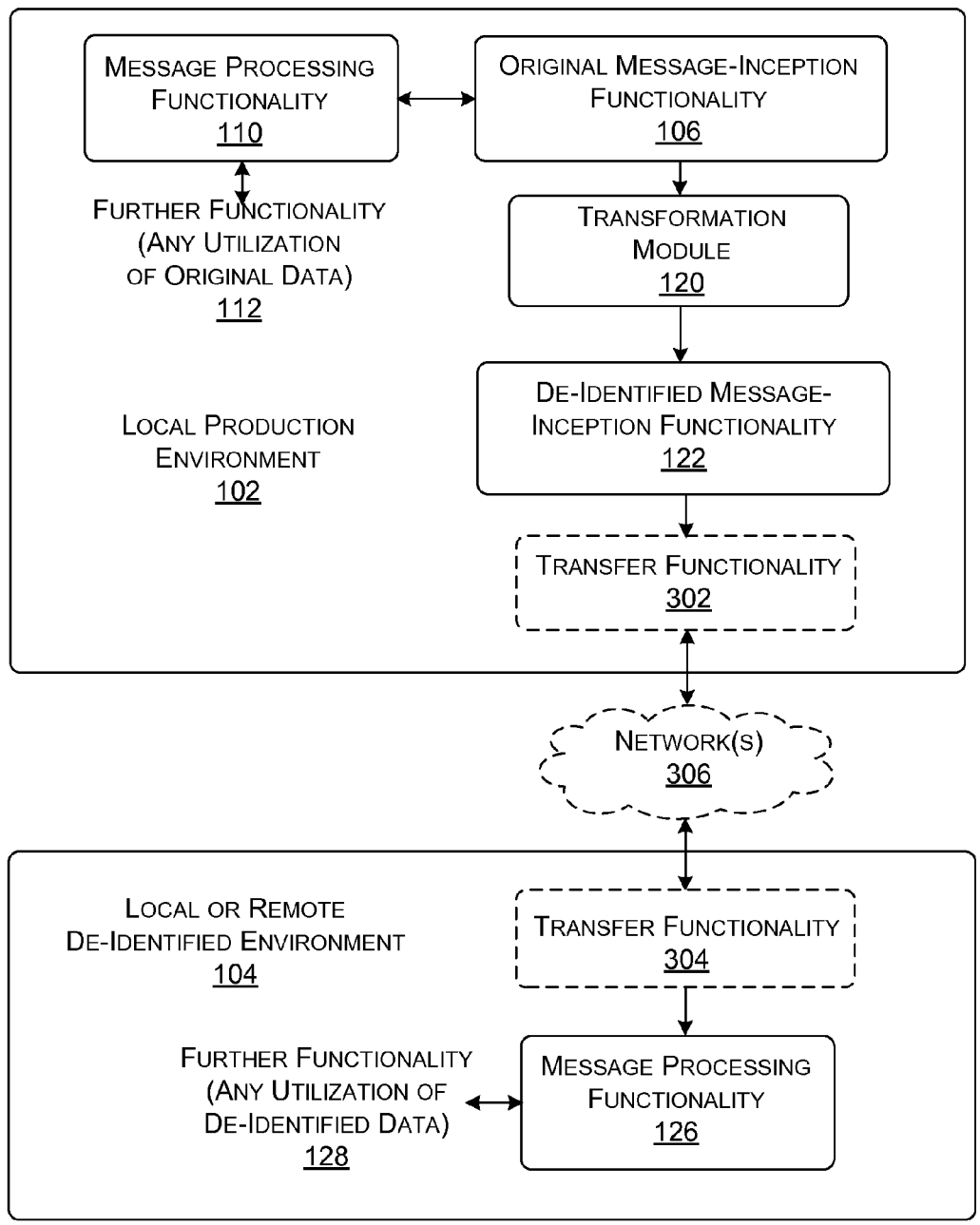
FIG. 3 shows an illustrative implementation of the de-identification system of FIG. 1.

FIG. 3 shows one implementation of the de-identification system 100 of FIG. 1. In this example, the local production environment 102 is coupled to a local or remote de-identified environment 104. The implementation can include transfer functionality (302, 304) for communicatively coupling the environments (102, 104) together, e.g., via one or more networks 306 or other coupling mechanism. If the de-identified environment 104 is local with respect to the production environment 102, then the transfer of de-identified messages can be performed in local fashion, e.g., without use of the network(s) 306.

The local production environment 102 can include the above-described original message-inception functionality 106, functionality (110, 112), transformation module 120, and de-identified message-inception functionality 122 for storing the de-identified messages produced by the transformation module 120. In this embodiment, the transfer functionality (302, 304) can transfer the de-identified messages from the production environment 102 to the de-identified environment 104, where they can be operated on by the functionality (126, 128) in any manner.

The implementation shown in FIG. 3 can be varied in different ways. For example, another implementation can perform the data sanitizing operation in the de-identified environment 104, instead of the production environment 102. In other words, such an implementation would provide the transformation module 120 in the de-identified environment 104, rather than the production environment 102.

Further, although not shown in FIG. 3, the de-identification system 100 can make use of other agents in transferring messages from the production environment 102 to the de-identified environment 104. For example, the examples of FIG. 3 can include one or more intermediary modules or systems, etc.

According to one use scenario, the production environment 102 shown in FIG. 3 can use the transfer functionality (302, 304) to transfer a corpus of messages to the de-identified environment 104. For example, such a corpus can correspond to original messages that have been collected by the production environment 102 over a defined span of time, e.g., days, months, years, etc. The transformation module 120 sanitizes the corpus of messages before they can be operated on by the processing functionality 122 of the de-identified environment 104, thus reducing the risk that sensitive information will be released to the downstream processing performed in the de-identified environment 104. In one implementation, the transfer, together with the transformation, can be performed in a substantially real-time manner (where real-time means that the transfer occurs in a manner that is synchronously responsive to an instruction to transfer the data). Hence, this transfer mechanism, together with the transformation module 120, acts as a transparent gateway for sending a sanitized version of the original messages to the de-identified environment 104. The recipients in the de-identified environment 104 may not be aware of the conversion that is performed in the course of message transfer (or prior to message transfer).

FIG. 4 shows one implementation of the original message-inception functionality 106 of FIG. 1. The original message-inception functionality 106 can include a message management module 402 which governs the manner in which original messages are stored within the original message-inception functionality 106. In one example, the message management module 402 can receive original messages from any source or combination of sources described above. The message management module 402 can store the original messages in both a working queue 404 and a backup queue 406. This can be done by replicating the original messages in any manner, and at any timing. As used herein, a message queue (or just queue) refers to any mechanism for storing a stream of messages that have been received.

The production environment 102 draws from the working queue 404 to fulfill its normal day-to-day processing of original messages. In contrast, the transformation module 120 may pull original messages from the backup queue 406, rather than the working queue 404. This provision may be useful so that the de-identifying process does not negatively impact the performance of the production environment 102.

In one implementation, the message management module 402 can remove the original messages from the working queue 404 and the backup queue 406 after a prescribed amount of time, such as, without limitation, 30 days. The message management module 402 can also store the original messages in a long-term archive queue 408. As the name suggestions, the long-term archive queue 408 stores the original messages for more extended periods of time (e.g., indefi- nitely), depending on the configuration instructions provided by a trusted entity. The de-identified message-inception functionality 122 can adopt a similar architecture to that described above (for the original message-inception functionality 106), or a different architecture.

The architecture of the original message-inception functionality 106 accommodates various usage scenarios. In one use case, the transformation module 120 is configured to produce a de-identified message when triggered by the receipt of an original message. As a result, the transformation module 120 can forward de-identified messages to the de-identified environment 104 at generally the same times that original messages are forwarded to the production environment 102. This manner of operation corresponds to a real-time mode of de-identification.

According to another usage scenario, a trusted entity associated with the de-identified environment 104 can instruct the transformation module 120 to perform de-identification on a corpus of original messages stored in the long-term archive queue 408. In one situation, these original messages may have never been subjected to any type of de-identification processing. In another case, the original messages may have been scrubbed in the past, but the trusted entity now desires to perform a different type of de-identification processing on the original messages. This approach to de-identification is advantageous because it flexibly accommodates de-identification demands that arise after the collection of the original messages. FIG. 3, as described above, shows an implementation that can be used to provide a corpus of de-identified messages to the de-identified environment 104.

In a similar manner, a trusted entity associated with the production environment 102 can retrieve original messages from the long-term archive queue 408 for any reason. For example, the trusted entity may wish to parse these original messages in a different manner than was previously performed.

Figure 5:
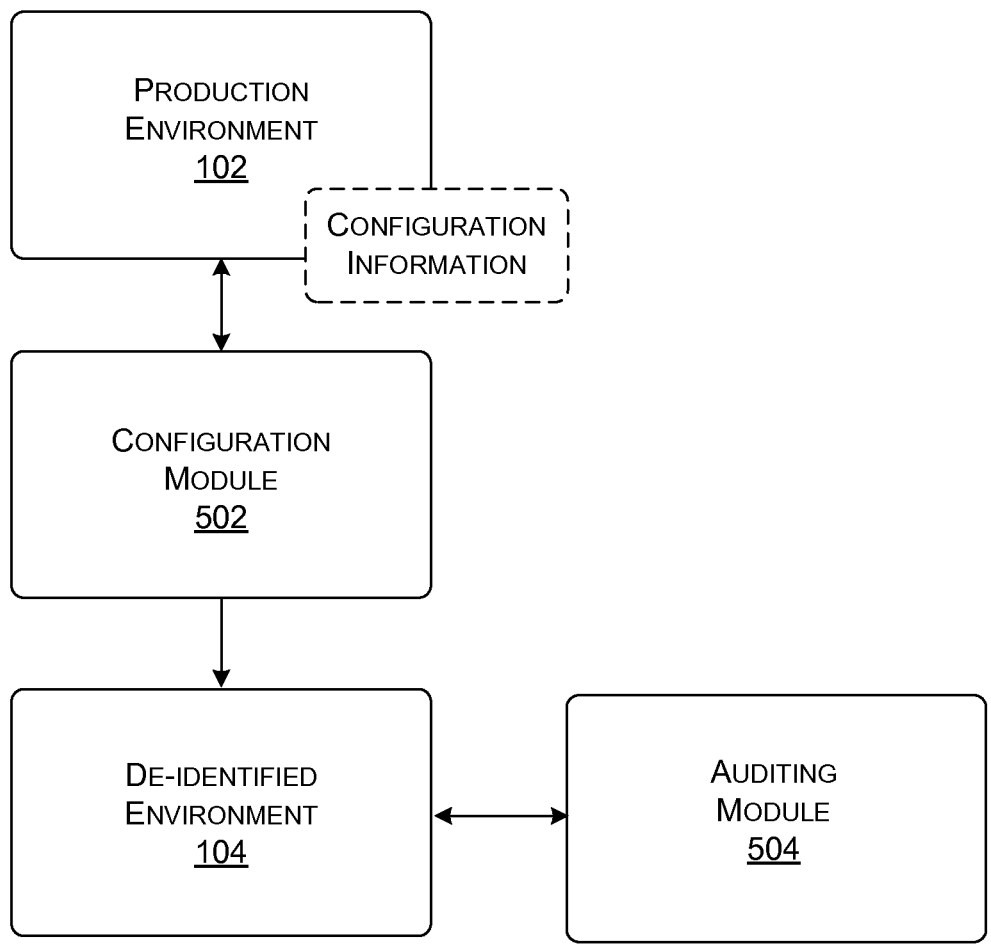
FIG. 5 shows illustrative configuration functionality and auditing functionality for use in the de-identification system of FIG. 1.

FIG. 5 shows supplemental functionality that can be used in the de-identification system 100 of FIG. 1. For example, the de-identification system 100 can include a configuration module 502 that operates to create the de-identified environment 104. For example, in one case, the configuration module 502 can build the de-identified environment 104 (or parts thereof) by copying the production environment 102 (or parts thereof). The configuration module 502 can generally perform this task by capturing configuration information which defines the configuration of at least parts of the production environment 102. For example, the configuration information can constitute application state information. The configuration module 502 can then use the configuration information to reconstitute a clone of the production environment 102 (or parts thereof) in the de-identified environment 104, e.g., by duplicating the application state information in the de-identified environment 104. However, as described above, the de-identified environment 104 can also include functionality and workflows that differ from the production environment 102 in any way.

More specifically, the configuration module 502 can resort to at least three approaches to build the de-identified environment 104. In a first approach, the configuration module 502 can provide tools which allow an authorized individual to manually install the de-identified environment 104, e.g., by manually creating a new system which duplicates the functions of the production environment 102. In a second approach, the configuration module 502 can provide tools for automatically (or semi-automatically) creating a virtual replication of the production environment 102 based on either a physical version of the production environment 102 or a virtual version of the production environment 102. A physical version corresponds to an implementation which is allocated to particular physical resources, such as particular computer servers. A virtual version corresponds to a virtual-level implementation which is flexibly allocated to a pool of underlying physical resources. The configuration module 502 can rely on any configuration functionality to perform this task, such as, for instance, Microsoft® System Center Virtual Machine Manager, or Hyper-V™, both produced by Microsoft® Corporation of Redmond, Wash.

The de-identification system 100 can also include an auditing module 504. The auditing module 504 can verify that the transformation module 120 has adequately removed sensitive information from the original messages. To perform this function, the auditing module 504 can maintain and apply verification rules. The verification rules embody the criteria by which a proper de-identification of an original message is evaluated. Those criteria may reflect the demands of a particular client and a particular legal jurisdiction.

In one scenario, the auditing module 504 can operate in real-time as the transformation module 120 operates on the original messages. For example, the auditing module 504 can determine, for each original message, whether the transformation module 120 has successfully converted instances of sensitive information to non-sensitive information. The auditing module 504 can make this assessment in view of the requirements of a particular jurisdiction and client. If the conversion does not meet this test, the auditing module 504 can generate an error message.

In another scenario, the auditing module 504 can operate on a corpus of de-identified messages that have already been converted by the transformation module 120, but have not yet been authorized for use by the de-identified environment 104. In another scenario, the auditing module 504 can examine de-identified data that is being used by the de-identified environment 104. Still other ways of integrating the auditing module 504 with the de-identification system 100 are possible.

Generally, the auditing module 504 can be administered by the same agent which operates the de-identified environment 104 (or the production environment 102), or a separate agent. The auditing operation, performed with the assistance of the auditing module 504, can be performed in a fully automatic manner, a semi-automatic manner, or a fully manual manner.

Figure 6:
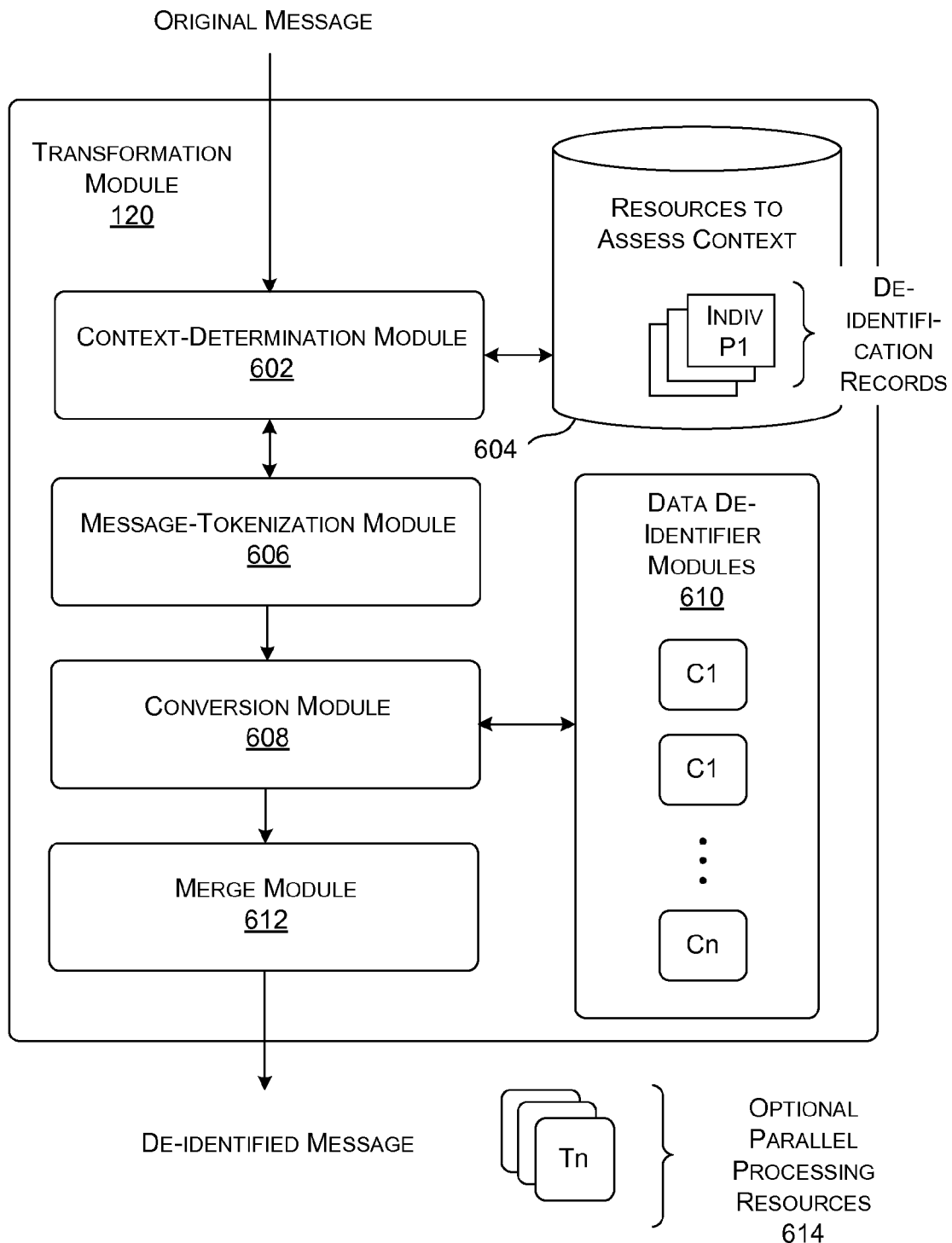
FIG. 6 shows an illustrative transformation module for use in the de-identification system of FIG. 1.

FIG. 6 shows one implementation of the transformation module 120 of FIG. 1. The transformation module 120 can include (or can be conceptualized to include) multiple sub-modules that perform different respective functions, as described below. The operations performed by the transformation module 120 are described with respect to a single original message which is converted into a de-identified message. However, the transformation module 120 can potentially operate on two or more original messages at the same time, e.g., by using multi-core technology, multi-threading technology, etc.

First, a context-determination module 602 can determine the context of an original message. As used herein, the context of an original message refers to any information that characterizes or categorizes the original message. For example the context-determination module 602 can determine that the original message conforms to a particular message type. If that conclusion can be reached, the context-determination module 602 can more accurately identify the different fields in the original message (insofar as each message type arranges information in a defined manner).

The context-determination module 602 can also extract information from the original message which identifies a person or person (or other entity) associated with the original message. For example, in a healthcare-related environment, the context-determination module 602 can extract information that identifies a patient from the original message. In one implementation, the context-determination module 602 can perform this task by first determining the type of message that has been received (as per the above-described processing); the context-determination module 602 can then extract the identity of the person from an appropriate field (or fields) in the original message.

After identifying the individual (or other entity), the context-determination module 602 can determine whether a de-identification record exists for this individual. The de-identification record (if it exists) would have been created upon first encountering a message pertaining to the individual. The de-identification record (if it exists) provides translation rules which identify the manner in which sensitive personal information items that pertain to this individual have been mapped to corresponding non-sensitive items. For example, the record may identify the manner in which the name of the individual has been translated into a fake name on past occasions, and so on. In one implementation, the transformation module 120 is configured to apply the translation rules identified in the de-identification record in processing the current original message pertaining to the individual. If no de-identification record exists for this individual (because messages pertaining to the individual have never been encountered before), then the context-determination module 602 can create and store a new record. The new de-identification record will be populated with appropriate translation rules, based on subsequent processing performed by the transformation module 120.

Generally, FIG. 6 indicates that the context-determination module 602 relies on one or more resources to perform the above-described tasks provided in one or more data stores 604. For example, the resources may provide criteria for use in classifying the type of the original message. The resources can also include the de-identification records for previously-encountered individuals.

A message-tokenization module 606 can then partition the original message into plural tokens, referred to herein as original message parts. The message-tokenization module 606 can perform this task in different ways. For example, if the context-determination module 602 is able to determine the type of the original message, the message-tokenization module 606 can partition the message into the fields that are found in that type of message. Alternatively, or in addition, the message-tokenization module 606 can provide techniques for detecting sensitive information in free-form message content. For example, the message-tokenization module 606 can identify and apply rules which detect name information, address information, social security number information, etc., based on typical patterns exhibited by these items. For example, the message-tokenization module 606 can identify nine-digit numbers as potentially referring to social security numbers, and so on.

A conversion module 608 can then convert each of the original message parts into respective transformed parts, assuming that the de-identification record does not already inform the conversion module 608 how this transformation is to be performed. The conversion module 608 performs this task by drawing on one or more data de-identifier modules in a suite 610 of data de-identifier modules. In some cases, a conversion module 608 can provide a transformation that simply passes an original message part through without modification. In other cases, a conversion module 608 can modify the original message part in any way summarized above. Namely, in some instances, the conversion module 608 can replace sensitive information with completely arbitrary information which has no relation to the original sensitive information. In other instances, the conversion module 608 can shift or otherwise vary the original sensitive information to produce the transformed message part. In other instances, the conversion module 608 can preserve higher-level properties of the original sensitive data, and so on. In one case, the suite 610 of data de-identifier modules can incorporate a pluggable approach that flexibly accommodates the introduction of new data de-identifier modules, including, optionally, commercially available data de-identifier modules produced by others. Some data de-identifier modules may themselves incorporate multiple component de-identifier modules for handling different data types or different data processing scenarios.

Finally, a merge module 612 can assemble the transformed message parts produced by the conversion module 608 into a de-identified message. In one implementation, the merge module 612 assembles the transformed message parts in an order which matches the order of the counterpart original message parts in the original message.

FIG. 6 also indicates that the functionality described above can be implemented by parallel processing resources 614. This means that the functionality can be replicated in any way, e.g., by using plural machines, plural processing cores and/or plural threads on a single machine, etc. In these cases, the transformation module 120 can operate on different streams of original messages in a parallel and distributed fashion.

B. Illustrative Processes

FIGS. 7-13 set forth procedures that explain the operation of the de-identification system 100 of FIG. 1 in flowchart form. Since the principles underlying the operation of the de-identification system 100 have already been described in Section A, certain operations will be addressed in summary fashion in this section.

Figure 7:
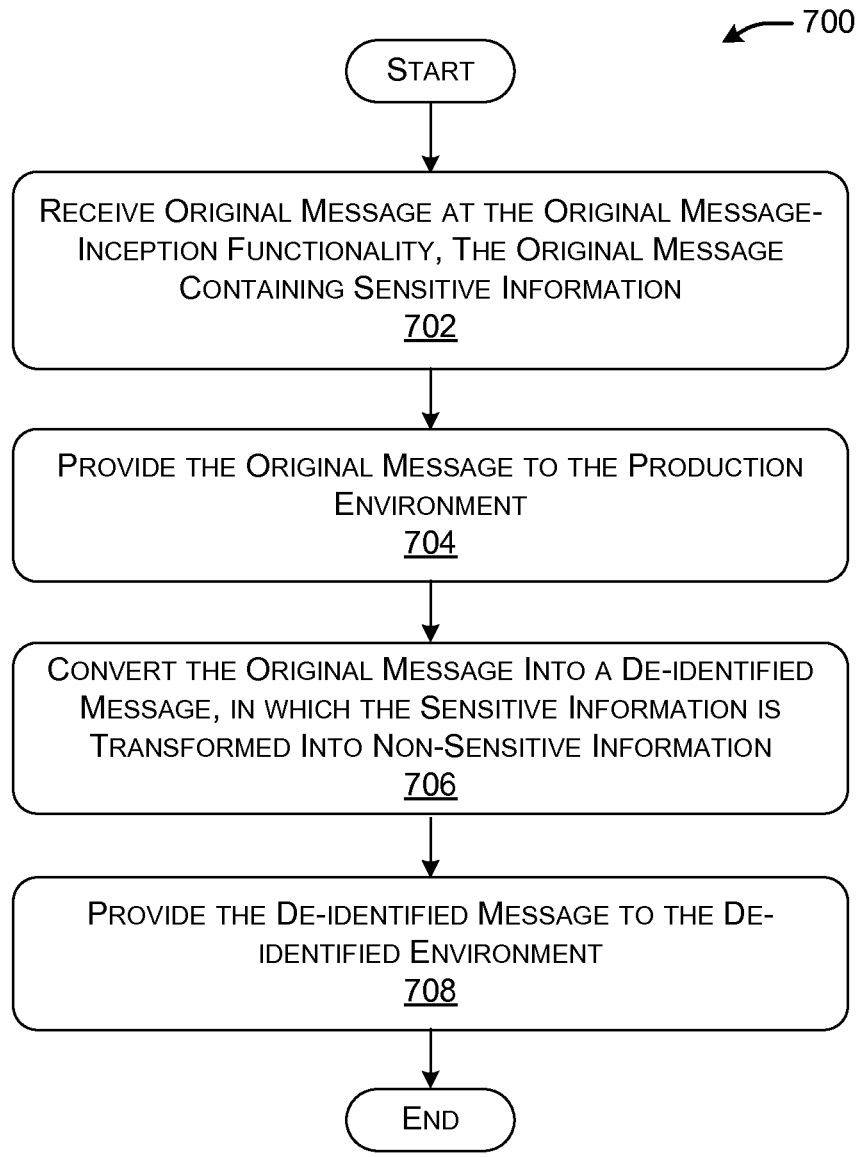
FIG. 7 is a flowchart that provides an overview of the one manner of operation of de-identification system of FIG. 1.

Starting with FIG. 7, this figure shows a procedure 700 which is an overview of one manner of operation of the de-identification system of FIG. 1. This procedure 700 is explained in the context of operations performed on a single original message. In block 702, the de-identification system 100 receives an original message at the original message-inception functionality 106. In block 704, the de-identification system 100 can provide the original message to the production environment 102. In block 706, the de-identification system 100 can use the transformation module 120 to convert the original message into a counterpart de-identified message. In block 708, the de-identification system 100 can provide the de-identified message to the de-identified environment 104. The de-identified environment 104 can be assured that the sensitive information has been removed from the original messages because this de-identification processing has been conducted prior to any complicating downstream processing performed in the production environment 102.

More specifically, the operation in block 706 can be performed in a synchronous real-time mode, e.g., in which the transformation is triggered by the receipt of the original message. The operation in block 706 can alternatively be performed in an asynchronous archival mode, e.g., in which the transformation occurs any time after the receipt of the original message (e.g., perhaps days, months, or years after the receipt and storage of the original message).

Figure 8:
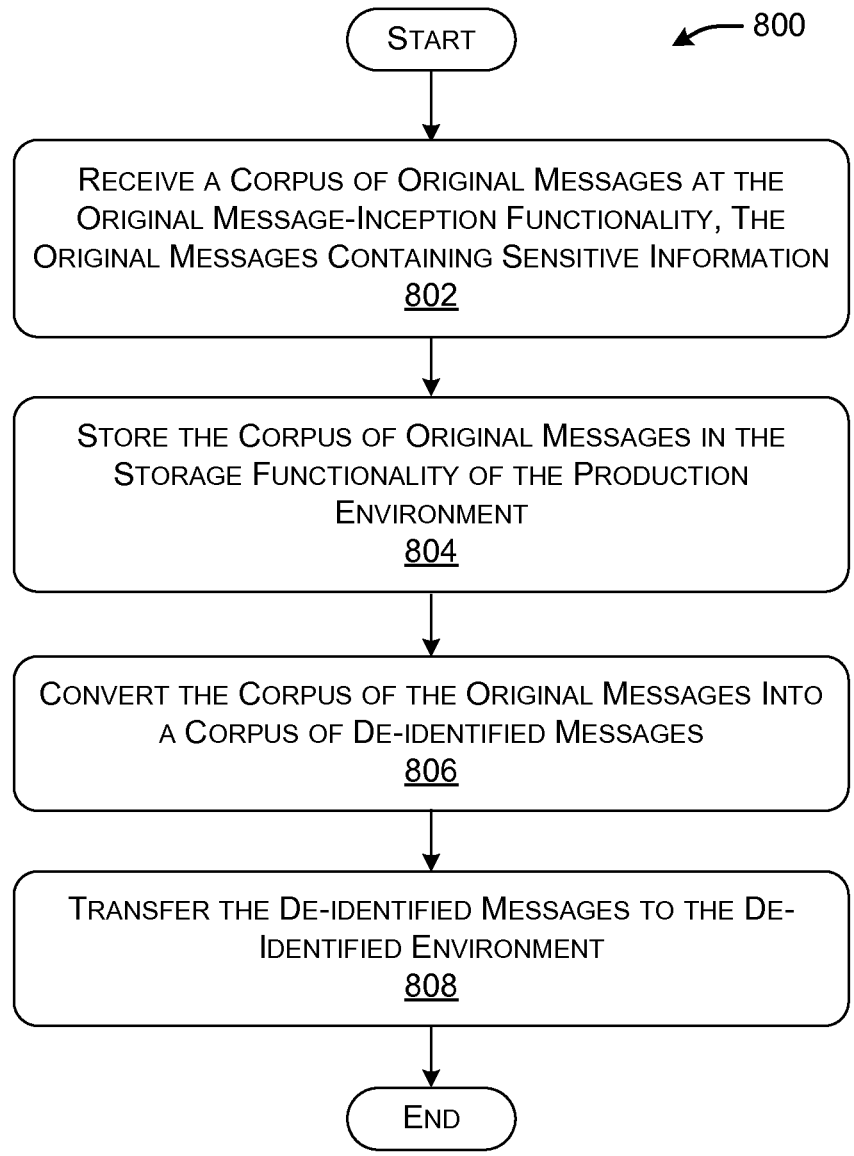
FIG. 8 is a flowchart that describes one implementation of the procedure shown in FIG. 7.

For example, FIG. 8 shows a procedure 800 which represents one implementation of the general protocol of FIG. 7. In block 802, the de-identification system 100 receives a corpus of original messages at the original message inception functionality 106. In block 804, the production environment 102 stores the original messages in its storage functionality 108. In block 806, the de-identification system 100 converts the corpus of original messages into a corpus of counterpart de-identified messages, which it stores in the storage functionality 124. In block 808, the de-identification system 100 transfers the corpus of de-identified messages to the de-identified environment 104.

Figure 9:
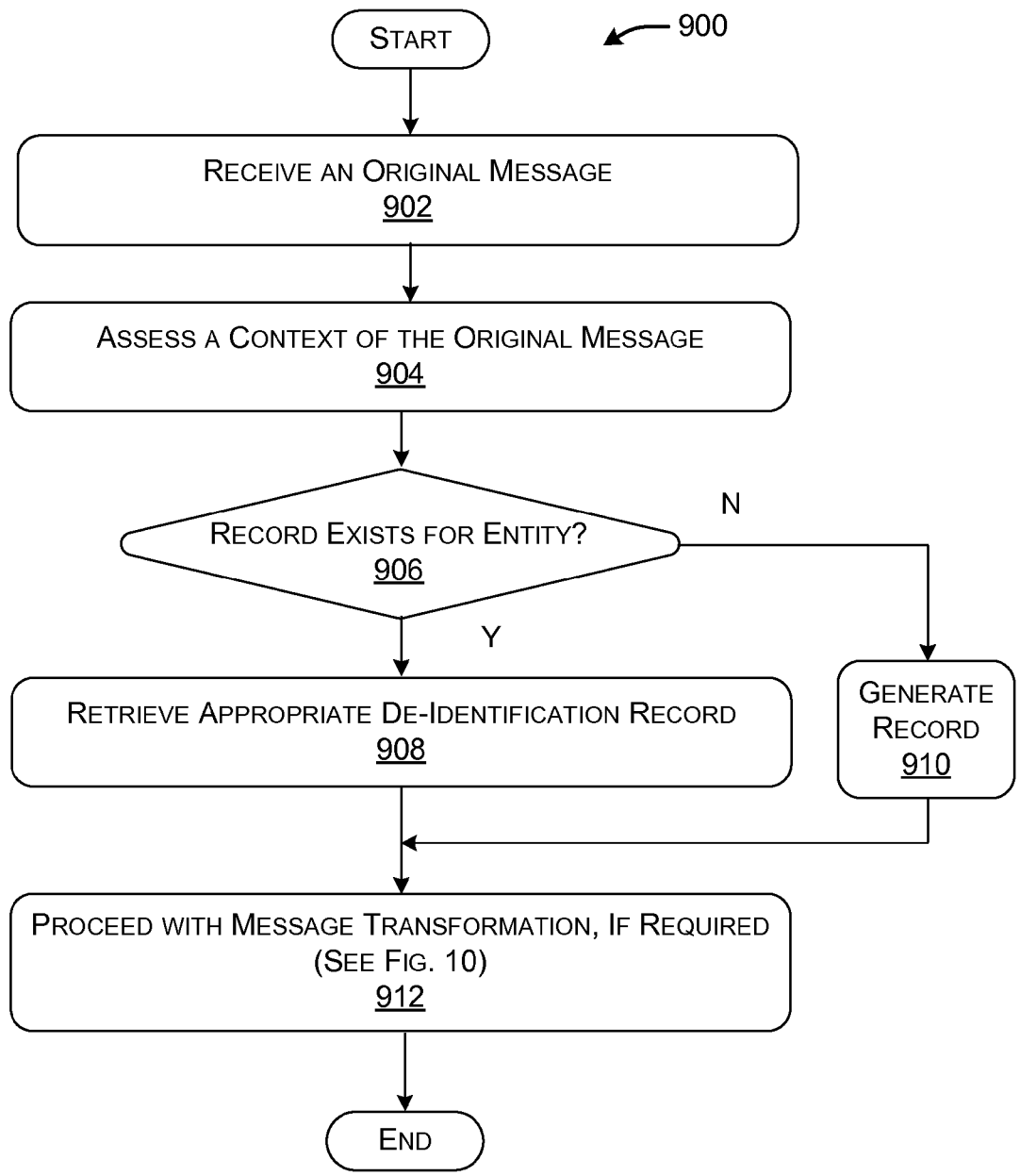
FIGS. 9 and 10 are flowcharts that together describe one manner of operation of the transformation module of FIG. 6.
Figure 10:
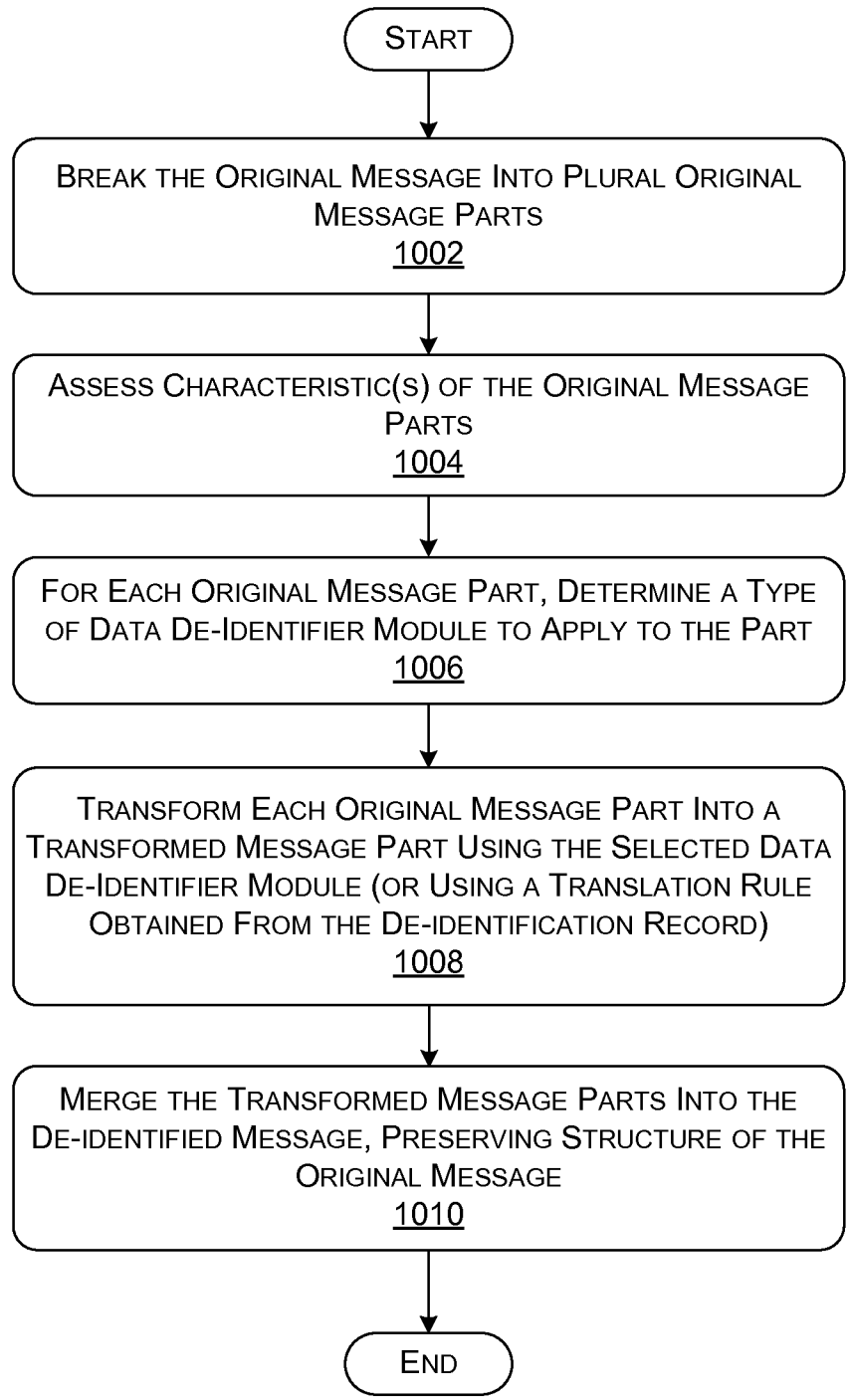

FIGS. 9 and 10 together show a procedure 900 which explains one manner of operation of the transformation module 120 shown in FIG. 6. This process is described with respect to the operations performed on a single original message. In block 902, the transformation module 120 receives an original message from the original message-inception functionality 106. In block 904, the transformation module 120 assesses the context of the original message. This operation, as described above, may entail identifying the type of message associated with the original message. This operation also may entail determining the person (or other entity) identified in the original message. In block 906, the transformation module 120 determines whether the original message identifies an individual for which a prior de-identification record exists. If so, in block 908, the transformation module 120 accesses the prior de-identification record. The prior de-identification record describes the manner in which sensitive information items associated with the individual have been previously mapped to non-sensitive information items (in the processing of prior messages pertaining to this individual). In one approach, if such a prior mapping exists, the transformation module 120 carries forward this same mapping when converting the current original message into a de-identified message. In block 910, if a prior de-identification record does not exist, the transformation module 120 creates one; such a record will initially include blank fields to be filled in as the de-identification process proceeds. Block 912 indicates that further transformation is next performed on the original message, as outlined in FIG. 10.

Namely, in block 1002 of FIG. 10, the transformation module 120 can break the original message into plural original message parts. This operation can be guided by the context information established in block 1004. In block 1104, the transformation module 120 can assess the characteristics of each original message part. Again, this operation can be informed by the context information established in block 904. In block 1006, the transformation module 120 can determine a type of data de-identifier module that is appropriate to apply to each original message part, based on the assessment made in block 1004. In block 1008, the transformation module 120 transforms each original message part into a corresponding transformed message part using an appropriate data de-identifier module. In block 1010, the transformation module 120 merges the transformed messages parts into the resultant de-identified message.

The processing shown in FIG. 10 follows a different flow if a translation rule already exists for a particular original message part. For example, assume that a de-identification record for an individual already indicates that the person's actual name (Susan Z. Johnson) is to be converted into the fake name (Sally M. Fenton). There is no need to perform block 1106 in this case. And in block 1108, the transformation module 120 will then directly apply the appropriate translation rule.

Figure 11:
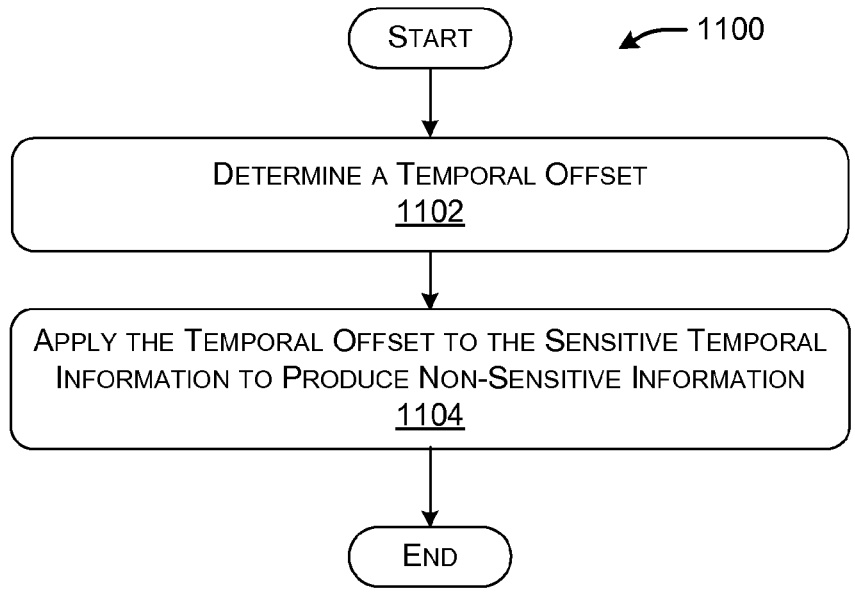
FIG. 11 is a flowchart that shows one manner of operation of a particular type of data de-identifier module used by the transformation module of FIG. 6.

FIG. 11 shows a procedure 1100 that explains the operation of one type of possible data de-identifier module. For instance, this type of data de-identifier module can be applied to temporal information of any type (e.g., dates, times, etc.). In block 1102, the data de-identifier module determines a temporal offset to apply to a particular sensitive information item. For example, in one approach, the transformation module 120 can assign a random number to each individual. The transformation module 120 can then define an offset that is based on the random number. For example assume that the offset is 16 and the individual is an elderly patient. The offset for that patient's date of birth may correspond to 16 months. If the same patient was a newborn infant, the offset might be 16 days, and so on. In block 1104, the data de-identifier module applies the temporal offset to the sensitive information items, e.g., by modifying the age of a patient by the temporal offset. This feature, as described above, helps preserve the privacy of the sensitive information while still retaining some context associated with the sensitive information.

The same type of shifting described above can be performed in other data domains that provide continuous data. For example, the transformation module 120 can assess the coordinates of a person's address. The transformation module 120 can then vary that address in any way, e.g., by selecting and applying an offset distance to the original address, to thereby find a new (nearby) address.

Figure 12:
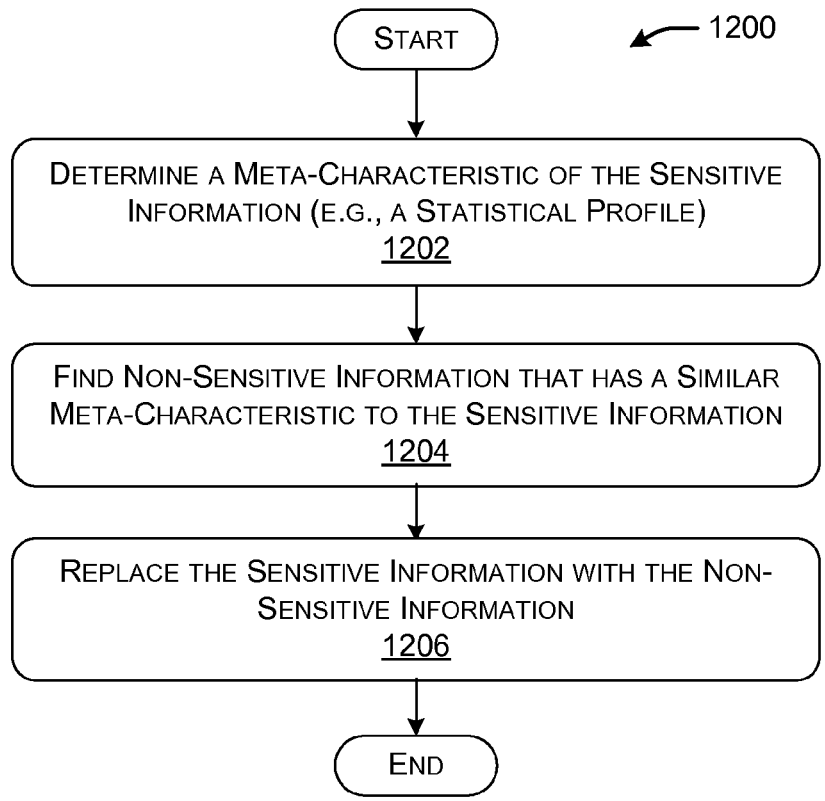
FIG. 12 is a flowchart that shows one manner of operation of another data de-identifier module used by the transformation module of FIG. 6.

FIG. 12 shows a procedure 1200 which explains the operation of another data de-identifier module. In block 1202, the data de-identifier module determines a meta-characteristic of an original sensitive information item, such as a statistical profile of the original sensitive information item. For example, the data de-identifier module can determine the prevalence of a name within a sample space, such as a census database. In block 1204, the data de-identifier module can then find a replacement item that has a similar meta-characteristic to the sensitive information item. In block 1206, the data de-identifier module can substitute the original sensitive information item with the replacement item. This procedure has the same advantages as the procedure 1100 of FIG. 11. Namely, the procedure 1200 preserves the privacy of the sensitive information, without purging the sensitive information of all its original high-level characteristics. For instance, this procedure will have the effect of replacing an unusual name with an equally unusual name.

Figure 13:
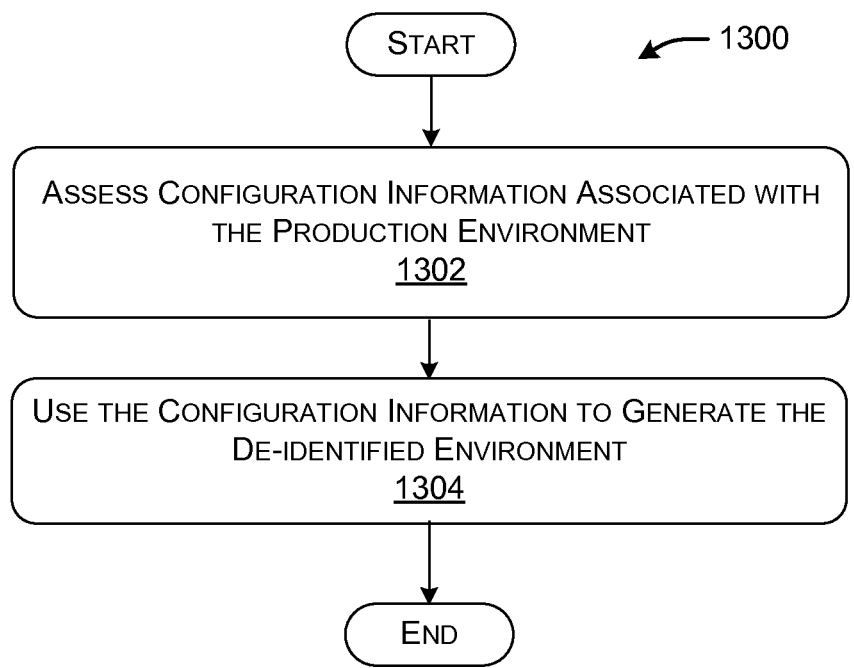
FIG. 13 is a flowchart that shows one manner of operation of a configuration module shown in FIG. 5.

FIG. 13 shows a procedure 1300 for providing the de-identified environment. In block 1302, the configuration module 502 (of FIG. 5) can determine configuration information that describes the configuration of the production environment 102. In block 1304, the configuration module 502 can use the configuration information to clone at least parts of the production environment 102 in the de-identified environment 104. Alternatively, or in addition, the de-identified environment 104 can include functionality that has no counterpart in the production environment 102, performing new functions or workflows that have no counterpart in the production environment 102.

C. Representative Processing Functionality

FIG. 14 sets forth illustrative electrical data processing functionality 1400 (also referred to herein a computing functionality) that can be used to implement any aspect of the functions described above. For example, the processing functionality 1400 can be used to implement any aspect of the de-identification system 100 of FIG. 1, e.g., as implemented in the embodiment of FIG. 3, or in some other embodiment. In one case, the processing functionality 1400 may correspond to any type of computing device that includes one or more processing devices. In all cases, the electrical data processing functionality 1400 represents one or more physical and tangible processing mechanisms.

The processing functionality 1400 can include volatile and non-volatile memory, such as RAM 1402 and ROM 1404, as well as one or more processing devices 1406 (e.g., one or more CPUs, and/or one or more GPUs, etc.). The processing functionality 1400 also optionally includes various media devices 1408, such as a hard disk module, an optical disk module, and so forth. The processing functionality 1400 can perform various operations identified above when the processing device(s) 1406 executes instructions that are maintained by memory (e.g., RAM 1402, ROM 1404, or elsewhere).

More generally, instructions and other information can be stored on any computer readable medium 1410, including, but not limited to, static memory storage devices, magnetic storage devices, optical storage devices, and so on. The term computer readable medium also encompasses plural storage devices. In all cases, the computer readable medium 1410 represents some form of physical and tangible entity.

The processing functionality 1400 also includes an input/output module 1412 for receiving various inputs (via input modules 1414), and for providing various outputs (via output modules). One particular output mechanism may include a presentation module 1416 and an associated graphical user interface (GUI) 1418. The processing functionality 1400 can also include one or more network interfaces 1420 for exchanging data with other devices via one or more communication conduits 1422. One or more communication buses 1424 communicatively couple the above-described components together.

The communication conduit(s) 1422 can be implemented in any manner, e.g., by a local area network, a wide area network (e.g., the Internet), etc., or any combination thereof The communication conduit(s) 1422 can include any combination of hardwired links, wireless links, routers, gateway functionality, name servers, etc., governed by any protocol or combination of protocols.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system comprising:
   a processing device configured to execute computer-executable instructions; and
   memory storing computer-executable instructions for:
   providing a quarantine domain within a local production environment, the quarantine domain including a message management module configured to receive an original message containing sensitive information from an external information source and store the original message containing the sensitive information in both a working queue and a backup queue within the quarantine domain, wherein the working queue stores the original message containing the sensitive information for processing by the local production environment;
   providing, within the quarantine domain, a transformation module configured to draw the original message containing the sensitive information from the backup queue, transform the original message into a counterpart de-identified message by converting the sensitive information in the original message into non-sensitive information, and store the counterpart de-identified message in a message queue within the quarantine domain, wherein:

the transformation module is triggered in response to receipt of the original message containing the sensitive information by the message management module, and the message queue stores the counterpart de-identified message for processing by a remote environment in which revelation of the sensitive information is not permitted.

2. The system of claim 1, wherein the transformation module transforms a corpus of original messages collected by the local production environment.

3. The system of claim 1, wherein the local production environment is configured to draw original messages from the working queue.

4. The system of claim 1, wherein the message management module is further configured to store original messages in an archive queue within the quarantine domain.

5. The system of claim 1, wherein the memory further stores computer-executable instructions for:

providing a configuration module configured to capture configuration information associated with the production environment and replicate at least partial functionality provided by the production environment in a de-identified environment in which revelation of the sensitive information is not permitted.

6. The system of claim 5, wherein the de-identified environment is local with respect to the production environment.

7. The system of claim 4-5, wherein:
the de-identified environment is remote with respect to the production environment and is coupled to the production environment via a network, and
the production environment includes transfer functionality for sending counterpart de-identified messages to the de-identified environment via the network.

8. The system of claim 1, wherein the transformation module is configured to transform original messages into counterpart de-identified messages using parallel processing resources.

9. The system of claim 1, wherein the transformation module comprises:
a context-determination module configured to provide context information for the original message;
a message-tokenization module configured to break the original message into plural original message parts based on the context information;
a conversion module configured to transform the original message parts into transformed message parts using respective data de-identifier modules; and
a merge module configured to merge the transformed message parts together to constitute the counterpart de-identified message.

10. A method comprising:
providing, on computing device, a quarantine domain within a local production environment, the quarantine domain including a message management module configured to receive an original message containing sensitive information from an external source;
storing, by the message management module, the original message in both a working queue and a backup queue within the quarantine domain, wherein the working queue stores the original message containing the sensitive information for processing by the local production environment;
providing, within the quarantine domain, a transformation module configured to draw the original message containing the sensitive information from the backup queue;

transforming, by the transformation module, the original message into a counterpart de-identified message by converting the sensitive information in the original message into non-sensitive information; and storing, by the transformation module, the counterpart de-identified message in a message queue within the quarantine domain, wherein:
the transformation module is triggered in response to receipt of the original message containing the sensitive information by the message management module, and
the message queue stores the counterpart de-identified message for processing by a remote environment in which revelation of the sensitive information is not permitted.

11. The method of claim 10, wherein the sensitive information pertains to a patient.

12. The method of claim 10, wherein the original message stored in the backup queue by the message management module is not subjected to any downstream processing by the production environment.

13. The method of claim 10, further comprising:
storing, by the message management module, the original message in an archive queue within the quarantine domain.

14. The method of claim 10, further comprising:
transforming, by the transformation module, a corpus of original messages collected by the production environment.

15. The method of claim 10, further comprising:
providing context information for the original message;
breaking the original message into plural original message parts based on the context information;
transforming the original message parts into corresponding transformed message parts using respective data de-identifier modules; and
merging the transformed message parts to produce the counterpart de-identified message.

16. The method of claim 10, wherein the sensitive information contains sensitive temporal information, and further comprising:
determining a temporal offset; and
applying the temporal offset to the sensitive temporal information to produce the non-sensitive information.

17. The method of claim 10, further comprising:
determining a meta-characteristic of the sensitive information;
finding similar non-sensitive information based on the meta-characteristic of the sensitive information; and
replacing the sensitive information with the similar non-sensitive information.

18. A computer-readable storage device storing computer-executable instructions that, when executed by one or more processing devices, cause the one or more processing devices to perform a method comprising:
providing a quarantine domain within a local production environment, the quarantine domain including a message management module configured to receive an original message containing sensitive information from an external source;
storing, by the message management module, the original message in both a working queue and a backup queue within the quarantine domain, wherein the working queue stores the original message containing the sensitive information for processing by the local production environment;

providing, within the quarantine domain, a transformation module configured to draw the original message containing the sensitive information from the backup queue;

transforming, by the transformation module, the original message into a counterpart de-identified message including non-sensitive information in place of the sensitive information; and storing, by the transformation module, the counterpart de-identified message in a message queue within the quarantine domain, wherein:

the transformation module is triggered in response to receipt of the original message containing the sensitive information by the message management module, and the message queue stores the counterpart de-identified message for processing by a remote environment in which revelation of the sensitive information is not permitted.

19. The computer-readable storage device of claim 18, wherein the sensitive information contains sensitive temporal information, and wherein the method further comprises:

determining a temporal offset; and applying the temporal offset to the sensitive temporal information to produce the non-sensitive information.

20. The computer-readable storage device of claim 18, wherein the method further comprises:

determining a statistical profile of the sensitive information;

finding similar non-sensitive information based on the statistical profile of the sensitive information; and replacing the sensitive information with the similar non-sensitive information.

* * * * *